United States Patent [19]
Böhner et al.

[11] 3,932,630
[45] Jan. 13, 1976

[54] TRIAZOLYL PHOSPHORUS ESTERS AS PESTICIDES

[75] Inventors: Beat Böhner, Binningen; Dag Dawes, Pratteln; Willy Meyer, Basel, all of Switzerland

[73] Assignee: Ciba-Geigy Corporation, Ardsley, N.Y.

[22] Filed: Dec. 6, 1974

[21] Appl. No.: 530,461

Related U.S. Application Data
[62] Division of Ser. No. 310,728, Nov. 30, 1972, Pat. No. 3,867,398.

[30] Foreign Application Priority Data
Dec. 10, 1971 Switzerland.................. 18064/71
Sept. 29, 1972 Switzerland.................. 14254/72

[52] U.S. Cl. ............................................. 424/200
[51] Int. Cl.² ........................................ A01N 9/36
[58] Field of Search ................................. 424/200

[56] References Cited
UNITED STATES PATENTS

| | | | |
|---|---|---|---|
| 3,686,200 | 8/1972 | Scherer et al. | 424/200 |
| 3,809,701 | 5/1974 | Dawes et al. | 424/200 |
| 3,862,124 | 1/1975 | Dawes et al. | 424/200 |
| 3,862,170 | 1/1975 | Dawes et al. | 424/200 |
| 3,862,957 | 1/1975 | Dawes et al. | 424/200 |
| 3,867,397 | 2/1975 | Bohner et al. | 260/308 R |

FOREIGN PATENTS OR APPLICATIONS

| | | | |
|---|---|---|---|
| 2,057,170 | 5/1971 | Germany | 260/308 |

OTHER PUBLICATIONS

Chem. Abst. 71101861(c) (1969), Abstract of S. African Patent 68/03,471 – 10-31-68.

*Primary Examiner*—Albert T. Meyers
*Assistant Examiner*—D. W. Robinson
*Attorney, Agent, or Firm*—Harry Falber

[57] ABSTRACT

Triazolylphosphorus compounds of the formula

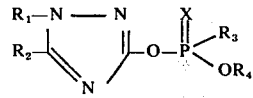

wherein
$R_1$ represents hydrogen, alkyl, cycloalkyl, phenyl, benzyl or phenethyl,
$R_2$ represents alkylthio, alkylsulphinyl, alkylsulphonyl, phenthio, phenylsulphinyl, phenylsulphonyl, benzylthio, benzylsulphinyl or benzylsulphonyl,
$R_3$ represents alkyl, alkoxy, alkylthio or phenyl,
$R_4$ represents alkyl, and
X represents oxygen or sulphur, processes for their production and their use for pest control.

12 Claims, No Drawings

TRIAZOLYL PHOSPHORUS ESTERS AS PESTICIDES

This is a division of application Serial No. 310,728, filed November 30, 1972, now U.S. Patent No. 3,867,398.

The present application relates to triazolylphosphorus compounds and to processes for their production, as well as to their use for pest control.

The triazolylphosphorus compounds correspond to the formula

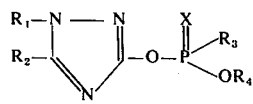
(I)

wherein
$R_1$ represents hydrogen, alkyl, cycloalkyl, phenyl, benzyl or phenethyl,
$R_2$ represents alkylthio, alkylsulphinyl, alkylsulphonyl, phenthio, phenylsulphinyl, phenylsulphonyl, benzylthio, benzylsulphinyl or benzylsulphonyl,
$R_3$ represents alkyl, alkoxy, alkylthio or phenyl,
$R_4$ represents alkyl, and
X represents oxygen or sulphur.

By the terms alkyl, alkoxy, alkylthio, alkylsulphinyl or alkylsulphonyl radical is meant in each case a straight-chain or branched radical having 1 to 12, preferably 1 to 6, carbon atoms, the said radical being unsubstituted or substituted by halogen, such as fluorine, chlorine, bromine and/or iodine, particularly fluorine or chlorine. Examples of such radicals are inter alia: methyl, methoxy, methylthio, methylsulphinyl, methylsulphonyl, ethyl, ethoxy, ethylthio, ethylsulphinyl, ethylsulphonyl, 2,2,2-trichloroethyloxy, 2,2,2-trifluorethyloxy, propyl, propoxy, n- and sec.-propylthio, propylsulphinyl, propylsulphonyl, n-butyl, n-butoxy, n-butylthio, i-, sec.-, tert.-butyl, n-pentyl, n-pentoxy, n-pentylthio.

The cycloalkyl radicals denoted by $R_1$ contain 3 to 8 ring carbon atoms. Preferred cycloalkyl radicals are cyclopropyl, cyclopentyl or cyclohexyl.

The phenyl, benzyl and phenethyl groups denoted by $R_1$ can be unsubstituted on the rings, or substituted, for example, by methoxy, halogen atoms such as fluorine, chlorine, bromine and/or iodine, preferably chlorine, and/or $C_1$–$C_5$-alkyl.

Of special importance because of their effectiveness are compounds of formula I wherein
$R_1$ represents hydrogen, $C_1$–$C_6$-alkyl, cyclopentyl, cyclohexyl, benzyl, phenethyl, phenyl, 3-chlorophenyl, 3-methylphenyl, 3-methyl-4-chlorophenyl, 2-methyl-4-chlorophenyl, 4-isopropylphenyl, 3-chloro-4-methoxyphenyl or 3,4-dichlorophenyl,
$R_2$ represents $C_1$–$C_5$-alkylthio, $C_1$–$C_5$-alkylsulphinyl, $C_1$–$C_5$-alkylsulphonyl, phenthio, phenylsulphinyl, phenylsulphonyl or benzylthio, benzylsulphinyl, benzylsulphonyl,
$R_3$ represents methyl, ethyl, methoxy, ethoxy, $C_1$–$C_5$-alkylthio or phenyl,
$R_4$ represents methyl, ethyl or propyl, and
X represents oxygen or sulphur.

The compounds can be produced by methods known per se, e.g. by the reaction of
a. a hydroxy-triazole of the formula

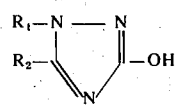
(II), in the presence of an acid-binding agent, with a compound of the formula

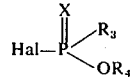
(III), or of
b. a hydroxy-triazole of the formula

(IV)

with a compound of the formula

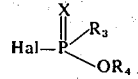
(III), wherein $R_1$ to $R_4$ and X have the meanings given for formula I, Hal stands for a halogen atom, particularly for chlorine or bromine, and Me stands for a monovalent metal, especially an alkali metal.

Suitable acid-binding agents are, for example, the following bases: tertiary amines such as triethylamine, dimethylaniline, pyridine, inorganic bases such as hydroxides and carbonates of alkali and alkaline-earth metals, preferably sodium and potassium carbonate.

The reactions are preferably carried out in solvents or diluents which are inert to the reactants. The following, for example, are suitable for this purpose: aromatic, hydrocarbons such as benzene, toluene, ligroins, halogenated hydrocarbons, chlorobenzene, polychlorobenzenes, bromobenzene, chlorinated alkanes having 1 to 3 carbon atoms; ethers such as dioxane, tetrahydrofuran; esters such as ethyl acetate; ketones such as acetone, methyl ethyl ketone, diethyl ketone, nitriles, e.g. acetonitrile, etc..

The starting materials of formulae II and IV are in some cases known compounds that can be produced, e.g. by a method analogous to that described in Chem. Ber. 56 B, 2276-83 (1923).

These compounds can be produced also by reaction of a 5-halogeno-3-hydroxy-1,2,4-triazole derivative with metal salts of mercaptans or thiophenols.

Finally, a number of these compounds can moreover be obtained by the reaction of 5-mercapto-3-hydroxy-1,2,4-triazole with an alkylating agent, such as, e.g. alkylhalide or a dialkylsulphate, in the presence of a base.

The compounds of formula I have a broad biocidal action, and can be used for the control of diverse plant and animal pests. The said compounds are suitable, in particular, for the control of insects of the families: Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleriidae, Culicidae, Tipulidae, Stomoxydae, Muscidae, Calliphoridae, Trypetidae, Pulicidae, as well as acarids of the families: Ixodidae, Argasidae, Tetranychidae, Dermanyssidae.

The insecticidal and/or acaricidal action can be substantially broadened and adapted to suit the particular circumstances by the addition of other insecticides and/or acaricides.

Suitable additives include, for example, the following active substances:

Organic phosphorus compounds

Bis-0,0-diethylphosphoric acid anhydride (TEPP)
Dimethyl-(2,2,2-trichloro-1-hydroxyethyl)-phosphonate (TRICHLORFON)
1,2-dibromo-2,2-dichloroethyldimethylphosphate (NALED)
2,2-dichlorovinyldimethylphosphate (DICHLORVOS)
2-methoxycarbamyl-1-methylvinyldimethylphosphate (MEVINPHOS)
Dimethyl-1-methyl-2-(methylcarbamoyl)-vinylphosphate cis (MONOCROTOPHOS)
3-(dimethoxyphosphinyloxy)-N,N-dimethyl-cis-crotonamide (DICROTOPHOS)
2-chloro-2-diethylcarbamoyl-1-methylvinyldimethylphosphate (PHOSPHAMIDON)
0,0-diethyl-0(or S)-2-(ethylthio)-ethylthiophosphate (DEMETON)
S-ethylthioethyl-0,0-dimethyl-dithiophosphate (THIOMETON)
0,0-diethyl-S-ethylmercaptomethyldithiophosphate (PHORATE)
0,0-diethyl-S-2-ethylthio)ethyldithiophosphate (DISULFOTON)
0,0-dimethyl-S-2-(ethylsulphinyl)ethylthiophosphate (OXYDEMETON METHYL)
0,0-dimethyl-S-(1,2-dicarbethoxyethyldithiophosphate (MALATHION)
0,0,0,0-tetraethyl-S,S'-methylene-bis-dithiophosphate (ETHION)
0-ethyl-S,S-dipropyldithiophosphate
0,0-dimethyl-S-(N-methyl-N-formylcarbamoylmethyl)-dithiophosphate (FORMOTHION)
0,0-dimethyl-S-(N-methylcarbamoylmethyl)dithiophosphate (DIMETHOATE)
0,0-dimethyl-0-p-nitrophenylthiophosphate (PARATHION-METHYL)
0,0-diethyl-0-p-nitrophenylthiophosphate (PARATHION)
0-ethyl-0-p-nitrophenylphenylthiophosphate (EPN)
0,0-dimethyl-0-(4-nitro-m-tolyl)thiophosphate (FENITROTHION)
0,0-dimethyl-0-2,4,5-trichlorophenylthiophosphate (RONNEL)
0-ethyl-0,2,4,5-trichlorophenylethylthiophosphate (TRICHLORONATE)
0,0-dimethyl-0-2,5-dichloro-4-bromophenylthiophosphate (BROMOPHOS)
0,0-dimethyl-0-(2,5-dichloro-4-jodphenyl)-thiophosphate (JODOFENPHOS)
4-tert. butyl-2-chlorophenyl-N-methyl-0-methylamidophosphate (CRUFOMATE)
0,0-dimethyl-0-(3-methyl-4-methylmercapto-phenyl)thiophosphate (FENTHION)
Isopropylamino-O-ethyl-0-(4-methylmercapto-3-methylphenyl)-phosphate 0,0-diethyl-0-p-(methylsulphinyl)phenyl-thiophosphate (FENSULFOTHION)
0-p-(dimethylsulphamido)phenyl-0,0-dimethylthiophosphate (FAMPHUR)
0,0,0',0'-tetramethyl-0,0'-thiodi-p-phenylenethiophosphate
0-ethyl-S-phenyl-ethyldithiophosphate
0,0-dimethyl-0-(α-methylbenzyl-3-hydroxy-crotonyl)phosphate
2-chloro-1-(2,4-dichlorophenyl)vinyl-diethylphosphate (CHLORFENVINPHOS)
1-chloro-1-(2,4,5-trichlorophenyl)vinyl-dimethylphosphate
0-[2-chloro-1 (2,5-dichlorophenyl)]vinyl-0,0-diethylthiophosphate
Phenylglyoxylonitriloxim-0,0-diethylthiophosphate (PHOXIM)
0,0-diethyl-0-(3-chloro-4-methyl-2-oxo-2-H-1-benzopyran -7-yl)-thiophosphate (COUMAPHOS)
2,3-p-dioxandithiol-S,S-bis(0,0-diethyldithiophosphate) (DIOXATHION)
5-[(6-chloro-2-oxo-3-benzoxazolinyl)methyl]0,0-diethyldithio-phosphate (PHOSALONE)
2-(diethoxyphosphinylimino)-1,3-dithiolane
0,0-dimethyl-S-[2-methoxy-1,3,4-thiadiazol-5-(4H)-onyl-(4)-methyl]dithiophosphate
0,0-dimethyl-S-phthalimidomethyl-dithiophosphate (IMIDAN)
0,0-diethyl-0-(3,5,6-trichloro-2-pyridyl)thiophosphate
0,0-diethyl-0-2-pyrazinylthiophosphate (THIONAZIN)
0,0-diethyl-0-(2-isopropyl-4-methyl-6-pyrimidyl)thiophosphate (DIAZINON)
0,0-diethyl-0-(2-chinoxalyl)thiophosphate
0,0-dimethyl-S-(4-oxo-1,2,3-benzotriazin-3(4H)-ylmethyl)-dithiophosphate (AZINPHOSMETHYL)
0,0-diethyl-S-(4-oxo-1,2,3-benzotriazin-3(4H)-ylmethyl)-dithiophosphate (AZINPHOSETHYL)
S-[(4,6-diamino-s-triazin-2-yl)methyl]-0,0-dimethyldithiophosphate (MENAZON)
0,0-dimethyl-0-(3-chloro-4-nitrophenyl)thiophosphate (CHLORTHION)
0,0-dimethyl-0( or S)-2-(ethylthioethyl)thiophosphate (DEMETON-S-METHYL)
2-(0,0-dimethyl-phosphoryl-thiomethyl)-5-methoxy-pyron-4-3,4-dichlorobenzyl-triphenylphosphonium chloride
0,0-diethyl-S-(2,5-dichlorophenylthiomethyl)dithiophosphate (PHENKAPTON)
0,0-diethyl-0-(4-methyl-cumarinyl-7-)-thiophosphate (POTASAN)
5-amino-bis(dimethylamido)phosphinyl-3-phenyl-1,2,4-triazole (TRIAMIPHOS)
N-methyl-5-(0,0-dimethylthiolphosphoryl)-3-thiavaleramide (VAMIDOTHION)
0,0-diethyl-0-[2-diemthylamino-4-methylpyrimidyl-(6)]-thiophosphate (DIOCTHYL)
0,0-dimethyl-S-(methylcarbamoylmethyl)-thiophosphate (OMETHOATE)
0-ethyl-0-(8-quinolinyl)-phenylthiophosphonate (OXINOTHIOPHOS)
0-methyl-S-methyl-amidothiophosphate (MONITOR)
0-methyl-0-(2,5-dichloro-4-bromophenyl)-benzothiophosphate (PHOSVEL)
0,0,0,0-tetrapropyldithiophosphate 3-(dimethoxyphosphinyloxy)-N-methyl-cis-crotonamide
0,0-dimethyl (N-ethylcarbamoylmethyl,dithiophosphate (ETHOATE-METHYL)
0,0-diethyl-S-(N-isopropylcarbamoylmethyl)-dithiophosphate (PROTHOATE)
S-N-(1-cyano-1-methylethyl)carbamoylmethyldiethylthiolphosphate (CYANTHOATE)
S-(2-acetamidoethyl)-0,0-dimethyldithiophosphate
Hexamethylphosphoric acid triamide (HEMPA)
0,0-dimethyl-0-(2-chloro-4-nitrophenyl)thiophosphate (DICAPTHON)
0,0-dimethyl-0-p-cyanophenyl thiophosphate (CYANOX)
0-ethyl-0-p-cyanophenylthiophosphonate
0,0-diethyl-0-2,4-dichlorophenylthiophosphate (DICHLORFENTHION)
0,2,4-dichlorophenyl-0-methylisopropylamidothiophosphate
0,0-diethyl-0-2,5-dichloro-4-bromophenylthiophosphate (BROMOPHOS-ETHYL)
Dimethyl-p-(methylthio)phenylphosphate
0,0-dimethyl-0-p-sulfamidophenylthiophosphate
0-[p-(p-chlorophenyl)azophenyl]0,0-dimethylthiophosphate (AZOTHOATE)
0-ethyl-S-4-chlorophenyl-ethyldithiophosphate
0-isobutyl-S-p-chlorophenyl-ethyldithiophosphate
0,0-dimethyl-S-p-chlorophenylthiophosphate
0,0-dimethyl-S-(p-chlorophenylthiomethyl)dithiophosphate
0,0-diethyl-p-chlorophenylmercaptomethyl-dithiophosphate (CARBOPHENOTHION)
0,0-diethyl-S-p-chlorophenylthiomethyl-thiophosphate
0,0-dimethyl-S-(carbethoxy-phenylmethyl)dithiophosphate (PHENTHOATE)
0,0-diethyl-S-(carbofluorethoxy-phenylmethyl)-dithiophosphate 0,0-dimethyl-S-carboisopropoxy-phenylmethyl)-dithiophosphate
0,0-diethyl-7-hydroxy-3,4-tetramethylene-coumarinyl-thiophosphate (COUMITHOATE)
2-methoxy-4-H-1,3,2-benzodioxaphosphorin-2-sulphide
0,0-diethyl-0-(5-phenyl-3-isooxazolyl)thiophosphate
2-(diethoxyphosphinylimino)-4-methyl-1,3-dithiolane
Tris-(2-methyl-1-aziridinyl)-phosphine oxide (METEPA)
S-(2-chloro-1-phthalimidoethyl)-0,0-diethyldithiophosphate
N-hydroxynaphthalimido-diethylphosphate
Dimethyl-3,5,6-trichloro-2-pyridylphosphate
0,0-dimethyl-0-(3,5,6-trichloro-2-pyridyl)thiophosphate
S-2-(ethylsulphonyl)ethyl dimethylthiolphosphate (DIOXYDEME-TON-S-METHYL)
Diethyl-S-2-(ethylsulphinyl)ethyl dithiophosphate (OXIDISULFONTON)
Bis-0,0-diethylthiophosphoric acid anhydride (SULFOTEP)
Dimethyl-1,3-di(carbomethoxy)-1-propen-2-yl-phosphate
Dimethyl-(2,2,2-trichloro-1-butyroyloxyethyl)phosphate (BUTONATE)
0,0-dimethyl-0-(2,2-dichloro-1-methoxy-vinyl)phosphate
Bis-(dimethylamido)fluorphophate (DIMEFOX)
3,4-dichlorobenzyl-triphenylphosphoniumchloride
-Dimethyl-N-methoxymethylcarbamoylmethyl-dithiophosphate (FORMOCARBAM)
0,0-diethyl-0-(2,2-dichloro-1-chloroethoxyvinyl)-phosphate
0,0-dimethyl-0-(2,2-dichloro-1-chloroethoxyvinyl)-phosphate
0-ethyl-S,S-diphenyldithiolphosphate
0-ethyl-S-benzyl-phenyldithiophosphonate
0,0-diethyl-S-benzyl-thiophosphate
0,0-dimethyl-S-(4-chlorophenylthiomethyl)dithiophosphate (METHYLCARBOPHENOTHION)
0,0-dimethyl-S-(ethylthiomethyl)dithiophosphate
Diisopropylaminofluorophosphate (MIPAFOX)
0,0-dimethyl-S-(morpholinylcarbamoylmethyl)dithiophosphate (MORPHOTHION)
Bismethylamido-phenylphosphate
0,0-dimethyl-S-(benzene sulphonyl)dithiophosphate
0,0-dimethyl-(S and O)-ethylsulphinylethylthiophosphate
0,0-diethyl-0-4-nitrophenylphosphate
Triethoxy-isopropoxy-bis(thiophosphinyl)disulphide
2-methoxy-(1,3,2,benzodioxaphosphate)-2-oxide
Octamethylpyrophosphoramide (SCHRADAN)
Bis (dimethoxythiophospphinylsulphido)-phenylmethane
N,N,N',N'-tetramethyldiamidofluorophosphate (DIMEFOX)
0-phenyl-0-p-nitrophenyl-methanthiophosphonate (COLEP)
0-methyl-0-(2-chloro-4-tert.butyl-phenyl)-N-methylamidothiophosphate (NARLENE)
0-ethyl-0-(2,4-dichlorophenyl)-phenylthiophosphonate
0,0-diethyl-0-(4-methylmercapto-3,5-dimethyl-phenyl)-thiophosphate
4,4'-bis-(0,0-dimethylthiophosphoryloxy)-diphenyl disulphide
0,0-di-(β-chloroethyl)-0-(3-chloro-4-methylcoumarinyl-7)-phosphate
S-(1-phthalimidoethyl)-0,0-diethyldithiophosphate
0,0-dimethyl-0-(3-chloro-4-diethylsulphamylphenyl)-thiophsophate
0-methyl-0-(2-carbisopropoxyphenyl)-amidothiophosphate
5-(0,0-dimethylphosphoryl)-6-chloro-bicyclo(3.2.0)-heptadiene (1,5)
0-methyl-0-(2-i-propoxycarbonyl-1-methylvinyl)-ethylamido-thiophosphate Nitrophenols and derivatives
4,6-dinitro-6-methylphenol, Na-salt [Dinitrocresol]
dinitrobutylphenol-(2,2',2''-triethanolamine salt
2-cyclohexyl-4,6-dinitrophenyl [Dinex]
2-(1-methylheptyl)-4,6-dinitrophenyl-crotonate [Dinocap]
2-sec.-butyl-4,6-dinitrophenyl-3-methyl-butenoate [Binapacryl]
2-sec.-butyl-4,6-dinitrophenyl-cyclopropionate
2-sec.-butyl-4,6-dinitrophenylisopropylcarbonate [Dinobuton]

Miscellaneous
pyrethin I
pyrethin II
3-allyl-2-methyl-4-oxo-2-cyclopentan-1-yl-chrysanthemumate (Allethrin)
6-chloriperonyl-chrysanthemumate (Barthrin)
2,4-dimethylbenzyl-chrysanthemumate (Dimethrin)
2,3,4,5-tetrahydrophthalimidomethylchrysanthemumate 4-chlorobenzyl-4-chlorophenylsulphide [Chlorobensid]
6-methyl-2-oxol, 3-dithiolo-[4,5-b]-quinoxaline (Quinomethionate)
(I)-3-(2-furfuryl)-2-methyl-4-oxocyclopent-2-enyl-(I)-(cis+trans)chrysanthemum-monocarboxylate [Furethrin]
2-pivaloyl-indane-1,3-dione [Pindon]
N'-(4-chloro-2-methylphenyl)-N,N-dimethylformamidine [Chlorophenamidin]
4-chlorobenzyl-4-fluorophenyl-sulphide [Fluorobenside]
5,6-dichloro-1-phenoxycarbanyl-2-trifluoromethyl-benzimidazole [Fenozaflor]
p-chlorophenyl-p-chlorobenzenesulphonate [Ovex]
p-chlorophenyl-benzenesulphonate [Fenson]
p-chlorophenyl-2,4,5-trichlorophenylsulphone [Tetradifon]
p-chlorophenyl-2,4,5-trichlorophenylsulphide [Tetrasul]
p-chlorobenzyl-p-chlorophenylsulphide [Chlorobenside]
2-thio-1,3-dithiolo-(,5-6)-quinoxaline [Thiochinox]
prop-2-ynyl-(4-t-butylphenoxy)-cyclohexylsulphite [Propargil].

Formamidines
1-dimethyl-2-(2'-methyl-4'-chlorophenyl)-formamidine (CHLORPHENAMIDIN)
1-methyl-2-(2'-methyl-4'-chlorophenyl)-formamidine
1-methyl-2-(2'-methyl-4'-bromophenyl)-formamidine
1-methyl-2-(2',4'-dimethylphenyl)-formamidine.
1-n-butyl-1-methyl-2-(2'-methyl-4'-chlorophenyl)-formamidine
1-methyl-1-(2'-methyl-4'-chloroaniline-methylene)-formamidine
2-(2''-methyl-4''-chlorophenyl)-formamidine
1-n-butyl-2-(2'-methyl-4'-chlorophenyl-imino)-pyrolidine.

Urea
N-2-methyl-4-chlorophenyl-N',N'-dimethyl-thiourea.

Carbamate
1-naphthyl-N-methylcarbamate (CARBARYL)
2-butinyl-4-chlorophenylcarbamate
4-dimethylamino-3,5-xylyl-N-methylcarbamate
4-dimethylamino-3-tolyl-N-methylcarbamate (AMINOCARB)
4-methylthio-3,5-xylyl-N-methylcarbamate (METHIOCARB)
3,4,5-trimethylphenyl-N-methylcarbamate
2-chlorophenyl-N-methylcarbamate (CPMC)
5-chloro-6-oxo-2-norborane-carbonitrile-0-)methylcarbamoyl)-oxime
1-(dimethylcarbamoyl)-5-methyl-3-pyrazolyl-N,N-dimethylcarbamate (DIMETILAN)
2,3-dihydro-2,2-dimethyl-7-benzofuranyl-N-methylcarbamate (CARBOFURAN)
2-methyl-2-methylthio-propionaldehyde-0-(methylcarbamoyl)-oxime (ALDICARB)
8-chinaldyl-N-methylcarbamate and their salts
methyl 2-isopropyl-4-(methylcarbamoyloxy)carbanilate
m-(1-ethylpropyl)phenyl-N-methylcarbamate
3,5-di-tert.butyl-N-methylcarbamate
m-(1-methylbutyl)phenyl-N-methylcarbamate
2-isopropylphenyl-N-methylcarbamate
2-sec.butylphenyl-N-methylcarbamate
m-tolyl-N-methylcarbamate
2,3-xylyl-N-methylcarbamate
3-isopropylphenyl-N-methylcarbamate
3-tert.butylphenyl-N-methylcarbamate
3-sec.butylphenyl-N-methylcarbamate
3-isopropyl-5-methylphenyl-N-methylcarbamate (PROMECARB)
3,5-diisopropylphenyl-N-methylcarbamate
2-chloro-isopropylphenyl-N-methylcarbamate
2-chloro-4,5-dimethylphenyl-N-methylcarbamate
2-(1,3-dioxolan-2-yl)phenyl-N-methylcarbamate (DIOXACARB)
2-(4,5-dimethyl-1,3-dioxolan-2-yl)phenyl-N-methylcarbamate
2-(1,3-dioxolan-2-yl)phenyl-N,N-dimethylcarbamate
2-(1,3-dithiolan-2-Yl)-N,N-dimethylcarbamate -yl)-N,N-dimethylcarbamate
2-(1,3-dithiolan-2-yl)phenyl-N,N-dimethylcarbamate
2-isopropoxyphenyl-N-methylcarbamate (APROCARB)
2-(2-propinyloxy)phenyl-N-methylcarbamate
3-(2-propinyloxy)phenyl-N-methylcarbamate
2-dimethylaminophenyl-N-methylcarbamate
2-diallylaminophenyl-N-methylcarbamate
4-diallylamino-3,5-xylyl-N-methylcarbamate (ALLYXICARB)
4-benzothienyl-N-methylcarbamate
2,3-dihydro-2-methyl-7-benzofuranyl-N-methylcarbamate
3-methyl-1-phenylpyrazol-5-yl-N,N-dimethylcarbamate
1-isopropyl-3-methylpyrazol-5-yl-N,N-dimethylcarbamate (ISOLAN)
2-dimethylamino-5,6-dimethylpyrimidin-4-yl-N,N-dimethyl-carbamate
3-methyl-4-dimethylaminomethyleneiminophenyl-N-methylcarbamate
3-dimethylamino-methyleneiminophenyl-N-methylcarbamate (FORMETANATE) and their salts
1-methylthio-ethylimino-N-methylcarbamate (METHOMYL)
2-methylcarbamoyloximino-1,3-dithiolane
5-methyl-2-methylcarbamoyloximino-1,3-oxythiolane
2-(1-methoxy-2-propoxy)phenyl-N-methylcarbamate
2-(1-butin-3-yl-oxy)phenyl-N-methylcarbamate
1-dimethyl-1-methylthio-0-methylcarbamyl-formoxime
1-(2'-cyanoethylthio)-0-methylcarbamyl-acetaldoxime
1-methylthio-0-carbamyl-acetaldoxime
0-(3-sec.butylphenyl)-N-phenylthio-N-methylcarbamate
2,5-dimethyl-1,3-dithioland-2-(0-methylcarbamyl)-aldoxime)
0-2-diphenyl-N-methylcarbamate
2-(N-methylcarbamyl-oximino)-3-chloro-bicyclo[2.2.1]heptane
2-(N-methylcarbamyl-oximino)-bicyclo[2.2.1]heptane
3-isopropylphenyl-N-methyl-N-chloroacetyl-carbamate
3-isopropylphenyl-N-methyl-N-methylthiomethyl-carbamate 0-(2,2-dimethyl-4-chloro-2,3-dihydro-7-benzofuranyl)-N-methylcarbamate
0-(2,2,4-trimethyl-2,3-dihydro-7-benzofuranyl)-N-methylcarbamate
0-naphthyl-N-methyl-N-acetyl-carbamate
0-5,6,7,8-tetrahydronaphthyl-N-methyl-carbamate
3-isopropyl-4-methylthio-phenyl-N-methylcarbamate
3,5-dimethyl-4-methoxy-phenyl-N-methylcarbamate
3-methoxymethoxy-phenyl-N-methylcarbamate
3-allyloxyphenyl-N-methylcarbamate
2-propargyloxymethoxy-phenyl-N-methyl-carbamate
2-allyloxyphenyl-N-methyl-carbamate
4-methoxycarbonylamino-3-isopropylphenyl-N-methyl-carbamate
3,5-dimethyl-4-methoxycarbonylamino-phenyl-N-methyl-carbamate
2-γ-methylthiopropylphenyl-N-methyl-carbamate
3-(α-methoxymethyl-2-propenyl)-phenyl-N-methyl-carbamate
2-chloro-5-tert.-butyl-phenyl-N-methyl-carbamate
4-(methyl-propargylamino)-3,5-xylyl-N-methyl-carbamate
4-(methyl-γ-chloroallylamino)-3,5-xylyl-N-methyl-carbamate
4-(methyl-β-chloroallylamino)-3,5-xylyl-N-methyl-carbamate
1-(β-ethoxycarbonalethyl)-3-methyl-5-pyrazolyl-N,N-dimethylcarbamate
3-methyl-4-(dimethylamino-methylmercapto-methyleneimino)phenyl-N-methylcarbamate
1,3-bis(carbamoylthio)-2-(N,N-dimethylamino)-propanehydrochloride
5,5-dimethylhydroresorcinoldimethylcarbamate
2-[ethyl-propargylamino]-phenyl-N-methylcarbamate
2-[methyl-propargylamino]-phenyl-N-methylcarbamate
2-[dipropargylamino]-phenyl-N-methylcarbamate
4-[dipropargylamino]-3-tolyl-N-methylcarbamate
4-[dipropargylamino]-3,5-xylyl-N-methylcarbamate
2-[allyl-isopropylamino]-phenyl-N-methylcarbamate
3-[allyl-isopropylamino]-phenyl-N-methylcarbamate Chlorinated Hydrocarbons
γ-hexachlorocyclohexane [GAMMEXANE; LINDAN: γ HCH]
1,2,4,5,6,7,8,8-octachloro-3α,4,7,7α'tetrahydro-4,7-methylenindane [CHLORDAN]
1,4,5,6,7,8,8-heptachloro,3α,4,7,7α-tetrahydro-4,7-methylenindane [HEPTACHLOR]
1,2,3,4,10,10-hexachloro-1,4,4α,5,8,8α-hexahydro-endo-1,4-exo-5,8-dimethanonaphthalene [ALDRIN]
1,2,3,4,10,10-hexachloro-6,7-epoxy-1,4,4α,5,6,7,8,8α-oxtahydro-exo-1,4-endo-5,8-dimethanonaphthalene [DIFLORIN]
1,2,3,4,10,10-hexachloro5,7-epxoy-1,4,4α,5,6,7,8,8α-octyhydro-endo-endo-5,8-dimethanonapthalene [ENDRIN]

In addition to possessing the above mentioned properties, the compounds of formula I are moreover effective against members of the division *Thallophyta*. Some of these compounds thus have a bactericidal action. They are, however, particularly effective against fungi, especially against the phytopathogenic fungi belonging to the following classes: Oomycetes, Zygomycetes, Ascomycetes, Basidiomycetes, Denteromycetes. The compounds of formula I also have a fungitoxic action in the case of fungi which attack the plants from the soil. Furthermore, the new active substances are suitable for the treatment of seed, fruit, tubers, etc., for protection against fungus infections. The compounds of formula I are suitable too for the control of phytopathological nematodes.

The compounds of formula I can be used on their own or together with suitable carriers and/or additives. Suitable carriers and additives may be solid or liquid, and correspond to the substances common in formulation practice, such as, e.g. natural and regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays, or solutions, the formulation of these preparations being effected in a manner commonly known in practice. Also to be mentioned are cattle dips and spray races, in which aqueous preparations are used.

The agents according to the invention are produced in a manner known per se by the intimate mixing and/or grinding of active substances of formula I with the suitable carriers, optionally with the addition of dispersing agents or solvents which are inert to the active substances. The active substances can be obtained and used in the following preparation forms:

solid preparations: dusts, scattering agents, granulates, coated granulates, impregnated granulates and homogeneous granulates;

liquid preparations:
a. water dispersible active substance concentrates: wettable powders, pastes, emulsions;
b. solutions.

The solid preparations (dusts, scattering agents) are produced by the mixing of the active substances with solid carriers. Suitable carriers are, e.g. kaolin, talcum, bole, loess, chalk, limestone, ground limestone, attapulgite, dolomite, diatomaceous earth, precipitated silicic acid, alkaline-earth silicates, sodium and potassium aluminium silicates (feldspar and mica), calcium and magnesium sulphates, magnesium oxide, ground synthetic materials, fertilisers such as ammonium sulphate, ammonium phosphate, ammonium nitrate, urea, ground vegetable products such as bran, dark dust, sawdust, ground nutshells, cellulose powder, residues of plant extractions, active charcoal, etc., alone or in admixture with each other.

Granulates can be very easily prepared by a process in which an active substance of formula I is dissolved in an organic solvent, the thus obtained solution applied to a granulated mineral, e.g. attapulgite, $SiO_2$, granicalcium, bentonite, etc., and the organic solvent then evaporated off.

It is possible also to produce polymer granulates; in this case the active substances of formula I are mixed with polymerisable compounds (urea/formaldehyde; dicyandiamide/formaldehyde; melamine/formaldehyde, or others); polymerisation is then carefully carried out in a manner which leaves the active substances unaffected, and granulation performed actually during the gel forming process. It is more favourable, however, to impregnate finished porous polymer granules (urea/formaldehyde, polyacrylonitrile, polyester and others), having a specific surface area and a favourable predeterminable adsorption/desorption ratio, with the active substances, e.g. in the form of their solutions (in a low-boiling solvent), and to then remove the solvent.

Polymer granulates of this kind can be also sprayed in the form of microgranulates, having bulk weights of preferably 300 g/liter to 600 g/liter, with the aid of spray apparatus. Spraying can be carried out over extensive areas of useful plant crops by the use of aeoplanes.

Granulates can also be obtained by the compacting of the carrier material with the active substances and additives, and a subsequent reducing operation.

Moreover, it is possible to add to these mixtures additives stabilising the active substance and/or non-ionic, anion-active and cation-active substances which improve, e.g. the adhesiveness of the active substances on plants and parts of plants (adhesives and agglutinants), and/or ensure a better wettability (wetting agents) as well as dispersibility (dispersing agents).

The following substances are, for example, suitable: olein/lime mixture, cellulose derivatives (methyl cellulose, carboxymethyl cellulose), hydroxyethylene glycol ethers of monoalkyl and dialkyl phenols having 5 to 15 ethylene oxide radicals per molecule and 8 to 9 carbon atoms in the alkyl radical, ligninsulphonic acid, the alkali metal and alkaline-earth metal salts thereof, polyethylene glycol ethers (carbowaxes), fatty alcohol polyglycol ethers having 5 to 20 ethylene oxide radicals per molecule and 8 to 18 carbon atoms in the fatty alcohol moiety, condensation products of ethylene oxide, propylene oxide, polyvinylpyrrolidones, polyvinyl alcohols, condensation products of urea and formaldehyde, as well as latex products.

Water-dispersible concentrates of active substances, i.e. wettable powders, pastes and emulsion concentrates, are agents which can be diluted with water to obtain any desired concentration. They consist of active substance, carrier, optionally additives which stabilise the active substance, surface-active substances, and anti-foam agents and, optionally, solvents.

The wettable powders and pastes are obtained by the mixing and grinding of the active substances with dispersing agents and pulverulent carriers, in suitable devices, until homogeneity is obtained. Suitable carriers are, e.g. those previously mentioned in the case of solid preparations. It is advantageous in some cases to use mixtures of different carriers. As dispersing agents it is possible to use, e.g.: condensation products of sulphonated naphthalene and sulphonated naphthalene derivatives with formaldehyde, condensation products of naphthalene or of naphthalenesulphonic acids with phenol and formaldehyde, as well as alkali, ammonium alkaline-earth metal salts of ligninsulphonic acid, also alkylarylsulphonates, alkali metal salts and alkaline-earth metal salts of dibutyl naphthalenesulphonic acid, fatty alcohol sulphates such as salts of sulphated hexadecanols, heptadecanols, octadecanols, and salts of sulphated fatty alcohol glycol ethers, the sodium salt of oleyl methyl tauride, ditertiary ethylene glycols, dialkyl dilauryl ammonium chloride, and fatty acid alkali-metal and alkaline-earth metal salts.

Suitable anti-foam agents are, e.g. silicones.

The active substances are so mixed, ground, sieved and strained with the above mentioned additives that the solid constituent in the case of wettable powders has a particle size not exceeding 0.02 to 0.04 mm, and in the case of pastes not exceeding 0.03 mm. For the preparation of emulsion concentrates and pastes, dispersing agents are used such as those mentioned in the preceding paragraphs, organic solvents and water. Suitable solvents are, e.g. alcohols, benzene, xylene, toluene, dimethylsulphoxide, and mineral oil fractions boiling in the range of 120° to 350°C. The solvents must be practically odourless, nonphytotoxic, and inert to the active substances.

Furthermore, the agents according to the invention can be used in the form of solutions. For this purpose, the active substance, or several active substances, of the general formula I is dissolved in suitable organic solvents, solvent mixtures, or water. As organic solvents it is possible to use aliphatic and aromatic hydrocarbons, their chlorinated derivatives, alkylnaphthalenes, mineral oils on their own or in admixture with each other.

The content of active substance in the above described agents is between 0.1 and 95%; it is to be mentioned in this connection that in the case of application of the agents from an aeroplane, or by means of some other suitable application devices, concentrations of up to 99.5% can be used, or even the pure active substance.

The active substances of formula I can be prepared, e.g. as follows:

Dusts:

The following substances are used for the preparation of a) 5% dust, and b) a 2% dust:

a. 5 parts of active substance
95 parts of talcum.

b. 2 parts of active substance
1 part of highly dispersed silicic acid
97 parts of talcum.

The active substances are mixed and ground with the carriers.

The following substances are used to produce a 5% granulate:

5 parts of active substance,
0.25 parts of epichlorhydrin,
0.25 parts of cetyl polyglycol ether,
3.50 parts of polyethylene glycol,
91 parts of kaolin (particle size 0.3 – 0.8 mm).

The active substance is mixed with epichlorhydrin and dissolved with 6 parts of acetone; The polyethylene glycol and cetyl polyglycol ether are then added. The thus obtained solution is sprayed on to kaolin, and the acetone subsequently evaporated in vacuo.

Wettable powder:

The following constituents are used for the preparation of a) a 40%, b) and c) a 25%, and d) a 10% wettable powder:

a. 40 parts of active substance,
5 parts of sodium lignin sulphonate,
1 part of sodium dibutyl-naphthalene sulphonate,
54 parts of silicic acid.

b. 25 parts of active substance,
4.5 parts of calcium lignin sulphonate
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 part of kaolin.

25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr, 46 parts of kaolin.

d. 10 parts active substance,
3 parts of a mixture of the sodium salts of saturated fatty alcohol sulphates,
5 parts of napthalenesulphonic acid/formaldehyde condensate,
82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates:

The following substances are used to produce a) a 10% and b) a 25% emulsifiable concentrate:

a. 10 parts of active substance,
3.4 parts of epoxidised vegetable oil,
13.4 parts of a combination emulsifier consisting of fatty alcohol polyglycol ether and alkylarylsulphonate calcium salt,
40 parts of dimethylformamide,
43.2 parts of xylene.

b. 25 parts of active substance,
2.5 parts of epoxidised vegetable oil,
10 parts of an alkylarylsulphonate/fatty alcohol-polyglycol ether mixture
5 parts of dimethylformamide,
57.5 parts of xylene.

From these concentrates it is possible to produce, by dilution with water, emulsions of any desired concentration.

Spray:

The following constituents are used to prepare a 5% spray:

5 parts of active substance,
1 part of epichlorhydrin,
94 parts of ligroin (boiling limits 160°–190°C).

EXAMPLE 1

Preparation of the starting materials a. 1-Isopropyl-5-methylmercapto-3-hydroxy-1,2,4-triazole An amount of 19.6 g of methylmercaptan is added at −5°C, with stirring, to 200 ml of 5N aqueous sodium hydroxide solution. An addition is then made of 33 g of 1-isopropyl-5-chloro-3-hydroxy-1,2,4-triazole, and the mixture heated for 2 hours at 100°C. After cooling to 20°C, the solution is acidified by the addition of potassium hydrogen sulphate, and extracted with ethyl acetate. The ethyl acetate extract is dried over anhydrous magnesium sulphate; it is then concentrated in a water-jet vacuum, and the residue crystallised from a little methanol at −70°C. The obtained product is 1-isopropyl-5-methylmercapto-3-hydroxy-1,2,4-triazole with a melting point of 90°–92°C.

The same compounds can be produced also as follows:

A mixture of 15.9 g of 1-isopropyl-5-mercapto-3-hydroxy-1,2,4-triazole, 11.1 g of triethylamine and 15.6 g of methyliodide in 100 ml of methanol is maintained for 4 hours at 40°C. The reaction mixture is concentrated to dryness in a water-jet vacuum; the residue is then taken up in 100 ml of water, and extracted twice with 200 ml of ethyl acetate each time. The organic phase is separated and concentrated by evaporation. There remains an amount of 16.5 g of crude 1-isopropyl-5-methylmercapto-1,2,4-triazole, which has, after recrystallisation from ether, a melting point of 90°–92°C.

b. 1-Phenyl-5-methylmercapto-3-hydroxy-1,2,4-triazole

An amount of 23.2 g of 1-phenyl-5-mercapto-1,2,4-triazole, M.P. 220°C, is placed into 50 ml of acetone, 50 ml of water and 10 ml of methyliodide. An addition is then made in portions, within 15 minutes, of 21 g of sodium carbonate, and, after completion of the addition, stirring continued for 1 hour at 30°C. The acetone is evaporated off, and the solution acidified with dilute hydrochloric acid. The precipitated product is filtered off, and recrystallised from 250 ml of ethanol to obtain 1-phenyl-5-methylmercapto-3-hydroxy-1,2,4-triazole in the form of white crystals having a melting point of 176°–177°C.

c. 1-Phenyl-5-methylsulphinyl-3-hydroxy-1,2,4-triazole

An amount of 41.4 g of 1-phenyl-5-methylmercapto-3-hydroxy-1,2,4-triazole is suspended at 50°C in 400 ml of ethyl acetate. An addition is then made dropwise, within 15 minutes, of 60 ml of a 60% solution of peroxyacetic acid in glacial acetic acid at 45°–50°C. After completion of the addition, the solution is stirred for 2 hours at 50°C, and the cooled to 20°C. The precipitated product is filtered off, washed with water, and dried in vacuo. The resulting product is 1-phenyl-5-methylsulphinyl-3-hydroxy-1,2,4-triazole in the form of white crystals, M.P. 180°–182°C.

d. 1-Phenyl-5-methylsulphonyl-3-hydroxy-1,2,4-triazole

An amount of 16.5 g of 1-phenyl-5-methylmercapto-3-hydroxy-1,2,4-triazole is suspended at 80°C in 200 ml of ethyl acetate; an addition is then made, in portions, of 30 ml of a solution of 60% peroxyacetic acid in glacial acetic acid. The solution, which has become clear after a certain time, is refluxed for 4 hours. After cooling to 10°C, the precipitated crystals are filtered off, washed with water and dried to thus obtain 1-phenyl-5-methylsulphonyl-3-hydroxy-1,2,4-triazole in the form of white crystals having a melting point of 173°–175°C.

e. 1-Isopropyl-5-phenyl-mercapto-3-hydroxy-1,2,4-triazole

Amounts respectively of 22 g of thiophenol, 16 g of sodium hydroxide and 32.3 g of 1-isopropyl-5-chloro-3-hydroxy-1,2,4-trizole in 40 ml of water are refluxed for three hours. The solution is thereupon cooled to 20°C, and acidified with hydrochloric acid to obtain a pH-value of 5. The precipitated oil is taken up in ethyl acetate. The solvent is evaporated off and the residue recrystallised from acetonitrile. The thus obtained product is 1-isopropyl-5-phenylmercapto-3-hydroxy-1,2,4-triazole in the form of colourless crystals having a melting point of 124°–126°C.

EXAMPLE 2

Preparation of the new phosphorus compounds a. 0,0-Diethyl-0-[1-isopropyl-5-methylmercapto-1,2,4-triazolyl-(3)]-thiophosphate Amounts respectively of 9.0 g of 1-isopropyl-5-methylmercapto-3-hydroxy-1,2,4-triazole, M.P. 90°–92°C, and 7.0 g of potassium carbonate in 250 ml of methyl ethyl ketone are refluxed for one hour. An addition is subsequently made dropwise at 50°C of 9.5 g of 0,0-diethyl-thiophosphoric acid chloride, and the mixture refluxed for two hours. After the precipitated salts have been filtered off and the solvent evaporated off in vacuo, there is obtained the compound of the formula

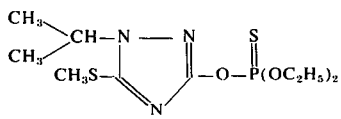

in the form of a pale yellow oil.

b. 0,0-diethyl-0-[1-methyl-5-isopropylmercapto-1,2,4-triazolyl-(3)]-thiophosphate Amounts of 8.9 g of 1-methyl-5-isopropylmercapto-3-hydroxy-1,2,4-triazole, M.P. 132°–135°C, and 7.0 g of potassium carbonate are refluxed in 300 ml of methyl ethyl ketone for two hours. The solution is cooled to room temperature and 9.8 g of 0,0-diethyl-thiophosphoric acid chloride then added. Refluxing is continued for one hour, and the solution afterwards stirred at room temperature. The precipitated salts are filtered off through Hyflo, and the solvent removed in vacuo from the clear filtrate; the residue remaining is the compound of the formula

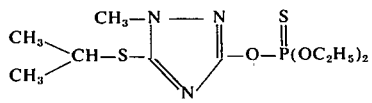

$n_D^{20} = 1,5085$ c. 0-Ethyl-0-[1-phenyl-5-methylmercapto-1,2,4-triazolyl-(3)]-ethyl-thiophosphonic acid ester Amounts of 20.7 g of 1-phenyl-5-methylmercapto-3-hydroxy-1,2,4-triazole, M.P. 176°–177°C, and 13.8 g of potassium carbonate in 500 ml of methyl ethyl ketone are refluxed for two hours. The solution is cooled to room temperature and an addition then made dropwise of 17.3 g of 0-ethyl-ethylthiophosphonic acid chloride; the mixture is subsequently refluxed for 2 hours. The precipitated salts are filtered off through Hyflo, and the filtrate concentrated in vacuo. The residue consists of the compound of the formula

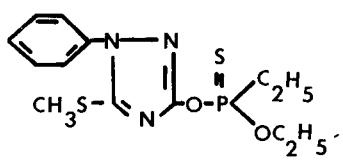

$n_D^{20} = 1,5699$ in the form of pale yellow oil.

d. 0,0-Dimethyl-0-[1-isopropyl-5-isopropylmercapto-1,2,4-triazolyl-(3)]-thiophosphate A mixture of 20.1 g of 1-isopropyl-5-isopropylmercapto-3-hydroxy-1,2,4-triazole, M.P. 130°–131°C, and 13.8 g of potassium carbonate in 500 ml of methyl ethyl ketone is refluxed for 2 hours, and then cooled to room temperature; an addition is subsequently made dropwise of 16.0 g of 0,0-dimethylthiophosphoric acid chloride, and the mixture afterwards stirred for 6 hours at 50°C and for 18 hours at 25°C. The precipitated salts are thereupon filtered off, and the solvent evaporated off in vacuo. After drying at 30°C/0.01 mm Hg, there is obtained the compound of the formula

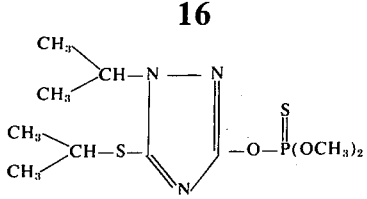

$n_D^{20} = 1,5082$ in the form of pale yellow oil.

e. 0,0-Diethyl-0-[1-phenyl-5-methylmercapto-1,2,4-triazolyl-(3)]-thiophosphate

A mixture consisting of 17.8 g of 1-phenyl-5-methylmercapto-3-hydroxy-1,2,4-triazole, 16.2 g of 0,0-diethylthiophosphoric acid chloride and 8.7 g of triethylamine in 200 ml of acetone is refluxed for 6 hours. The precipitated salts are separated, and the solvent evaporated off in vacuo. The residue is taken up in 250 ml of ethyl acetate, and washed with dilute hydrochloric acid and water. The solvent is evaporated off to thus obtain the compound of the formula

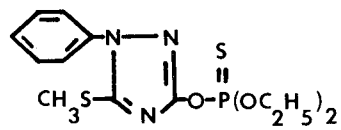

$n_D^{20} = 1,5625$ in the form of pale yellow oil.

f. 0,0-Diethyl-0-[5-isopropyl-mercapto-1,2,4-triazolyl-(3)]-thiophosphate

A mixture consisting of 19.1 g of 5-isopropylmercapto-3-hydroxy-1,2,4-triazole, M.P. 139°–141°C, and 18.2 g of potassium carbonate in 250 ml of acetonitrile is refluxed for half an hour. An addition is then made dropwise within 10 minutes of 22.6 g of 0,0-diethyl-thiophosphoric acid chloride at a temperature of 50°–55°C, and stirring subsequently carried out for 10 hours at 60°–65°C. After cooling to 20°C, the precipitated salts are filtered off. The solvent is evaporated off in vacuo, the crude product chromatographed through silica gel, and the compound of the formula

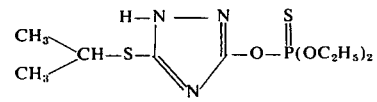

$n_D^{20} = 1,5159$ obtained as pale yellow oil.

g. 0,0-Diethyl-0-[1-phenyl-5-methylsulphinyl-1,2,4-triazolyl-(3)-thiophosphate )]-thiophosphate 18.0 g of 1-phenyl-5-methylsulphinyl-3-hydroxyl-1,2,4-triazole, M.P. 175°C, and 11.1 g of potassium carbonate in 500 ml of acetonitrile are refluxed for 2 hours, and then cooled to 40°C. An addition is made dropwise of 15.2 g of 0,0-diethyl-thiophosphoric acid chloride, and the mixture again refluxed for 2 hours. The undissolved salts are filtered off and the solvent then evaporated off in vacuo to obtain the compound of the formula

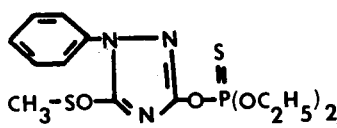

$n_D^{20} = 1,5551$ in the form of pale yellow oil.

h. 0,0-Diethyl-0-[1-phenyl-5-methylsulphonyl-1,2,4-triazolyl-(3)]-thiophosphate

An amount of 5.0 g of 1-phenyl-5-methylsulphonyl-3-hydroxy-1,2,4-triazole, M.P. 173°–175°C, together with 2.7 g of sodium carbonate is refluxed for 1½ 1/2 hours. An addition is made at 35°C of 4.0 g of 0,0-diethylthiophosphoric acid chloride. After 2 hours' refluxing, the precipitated salts are separated through Hyflo, and concentration in vacuo performed. There is thus obtained as residue the compound of the formula

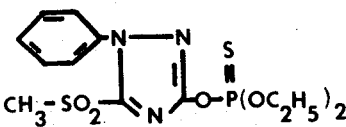

$n_D^{20} = 1,5380$ in the form of yellow oil.

The following compounds are obtained in an analogous manner:

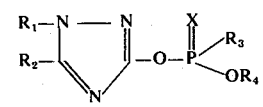

| R₁ | R₂ | R₃ | R₄ | X | Physical data |
|---|---|---|---|---|---|
| CH₃ | CH₃S | C₂H₅O | C₂H₅ | S | |
| CH₃ | CH₃SO | C₂H₅O | C₂H₅ | S | |
| CH₃ | CH₃SO₂ | C₂H₅O | C₂H₅ | S | |
| CH₃ | CH₃S | CH₃O | CH₃ | S | |
| CH₃ | CH₃S | (n)C₃H₇S | C₂H₅ | S | |
| CH₃ | CH₃S | C₂H₅ | C₂H₅ | S | |
| CH₃ | CH₃S | CH₃ | C₂H₅ | S | |
| CH₃ | CH₃S | CH₃ | (n)C₃H₇ | S | |
| CH₃ | CH₃S | (n)C₅H₁₁S | C₂H₅ | S | |
| CH₃ | CH₃S | (n)C₃H₇S | C₂H₅ | O | |
| CH₃ | CH₃S | ⌬ | C₂H₅ | S | |
| CH₃ | CH₃S | CH₃S | C₂H₅ | S | |
| CH₃ | C₂H₅S | C₂H₅O | C₂H₅ | S | |
| CH₃ | C₂H₅S | CH₃O | CH₃ | S | |
| CH₃ | C₂H₅S | (n)C₃H₇S | C₂H₅ | S | |
| CH₃ | C₂H₅S | C₂H₅ | C₂H₅ | S | |
| CH₃ | C₂H₅S | CH₃ | C₂H₅ | S | |
| CH₃ | C₂H₅S | CH₃ | (n)C₃H₇ | S | |
| CH₃ | Cl—CH₂—CH₂—S | C₂H₅O | C₂H₅ | S | |
| CH₃ | Cl—CH₂—CH₂—S | CH₃O | CH₃ | S | |
| CH₃ | Cl—(CH₂—CH₂—S | (n)C₃H₇S | C₂H₅ | S | |
| CH₃ | Cl—CH₂—CH₂—S | C₂H₅ | C₂H₅ | S | |
| CH₃ | (n)C₃H₇S | C₂H₅O | C₂H₅ | S | |
| CH₃ | (n)C₃H₇S | CH₃O | CH₃ | S | |
| CH₃ | (n)C₃H₇S | (n)C₃H₇S | C₂H₅ | S | |
| CH₃ | (n)C₃H₇S | C₂H₅ | C₂H₅ | S | |
| CH₃ | (i)C₃H₇S | CH₃O | CH₃ | S | |
| CH₃ | (i)C₃H₇S | (n)C₃H₇S | C₂H₅ | S | |
| CH₃ | (i)C₃H₇S | C₂H₅ | C₂H₅ | S | |
| CH₃ | (i)C₃H₇S | C₂H₅O | C₂H₅ | O | $n_D^{20}$: 1,4791 |
| CH₃ | (i)C₃H₇S | CH₃ | (n)C₃H₇ | S | |
| CH₃ | (i)C₃H₇S | CH₃ | C₂H₅ | S | |
| CH₃ | (n)C₄H₉S | C₂H₅O | C₂H₅ | S | |
| CH₃ | (n)C₄H₉S | CH₃O | CH₃ | S | |
| CH₃ | (n)C₄H₉S | (n)C₃H₇S | C₂H₅ | S | |
| CH₃ | (n)C₄H₉S | C₂H₅ | C₂H₅ | S | |
| CH₃ | (i)C₄H₉S | C₂H₅O | C₂H₅ | S | |
| CH₃ | (i)C₄H₉S | CH₃O | CH₃ | S | |
| CH₃ | (i)C₄H₉S | (n)C₃H₇S | C₂H₅ | S | |
| CH₃ | (i)C₄H₉S | C₂H₅ | C₂H₅ | S | |
| CH₃ | sec. C₄H₉S | C₂H₅O | C₂H₅ | S | |
| CH₃ | sec. C₄H₉S | CH₃O | CH₃ | S | |
| CH₃ | sec. C₄H₉S | (n)C₃H₇S | C₂H₅ | S | |
| CH₃ | sec. C₄H₉S | C₂H₅ | C₂H₅ | S | |
| CH₃ | tert.C₄H₉S | C₂H₅O | C₂H₅ | S | |
| CH₃ | tert.C₄H₉S | CH₃O | CH₃ | S | |
| CH₃ | tert.C₄H₉S | (n)C₃H₇S | C₂H₅ | S | |
| CH₃ | ⌬-CH₂-SO | C₂H₅ | C₂H₅ | S | |
| CH₃ | ⌬-CH₂-SO₂ | C₂H₅O | C₂H₅ | S | |
| CH₃ | (t)C₄H₉S | C₂H₅ | C₂H₅ | S | |
| CH₃ | (n)C₅H₉S | C₂H₅O | C₂H₅ | S | |
| CH₃ | (n)C₁₂H₂₅S | C₂H₅O | C₂H₅ | S | |
| CH₃ | (n)C₁₂H₂₅S | CH₃O | CH₃ | S | |
| CH₃ | Cl—CH₂—CH₂—CH₂S | C₂H₅O | C₂H₅ | S | |
| CH₃ | Cl—CH₂—CH₂—CH₂S | CH₃O | CH₃ | S | |
| CH₃ | ⌬-S | C₂H₅O | C₂H₅ | S | |
| CH₃ | ⌬-S | CH₃O | CH₃ | S | |

-continued

| R₁ | R₂ | R₃ | R₄ | X | Physical data |
|---|---|---|---|---|---|
| CH₃ | C₆H₅-SO | C₂H₅O | C₂H₅ | S | |
| CH₃ | C₆H₅-SO₂ | C₂H₅O | C₂H₅ | S | |
| CH₃ | C₆H₅-CH₂-S | C₂H₅O | C₂H₅ | S | |
| CH₃ | C₆H₅-CH₂-S | CH₃O | CH₃ | S | |
| C₂H₅ | CH₃S | C₂H₅O | C₂H₅ | S | |
| C₂H₅ | CH₃S | CH₃O | CH₃ | S | |
| C₂H₅ | CH₃S | (n)C₃H₇S | C₂H₅ | S | |
| C₂H₅ | CH₃S | C₂H₅ | C₂H₅ | S | |
| C₂H₅ | CH₃S | CH₃ | (n)C₃H₇ | S | |
| C₂H₅ | CH₃S | C₆H₅ | C₂H₅ | S | |
| C₂H₅ | C₂H₅S | C₂H₅O | C₂H₅ | S | |
| C₂H₅ | C₂H₅S | CH₃O | CH₃ | S | |
| C₂H₅ | C₂H₅S | (n)C₃H₇S | C₂H₅ | S | |
| C₂H₅ | C₂H₅S | C₂H₅ | C₂H₅ | S | |
| C₂H₅ | C₂H₅S | CH₃ | C₂H₅ | S | |
| C₂H₅ | C₂H₅S | CH₃ | (n)C₃H₇ | S | |
| C₂H₅ | C₂H₅S | (n)C₃H₇S | C₂H₅ | O | |
| C₂H₅ | C₂H₅SO | C₂H₅O | C₂H₅ | S | |
| C₂H₅ | (n)C₃H₇S | C₂H₅O | C₂H₅ | S | |
| C₂H₅ | (i)C₃H₇S | C₂H₅O | C₂H₅ | S | |
| C₂H₅ | (i)C₄H₉S | C₂H₅O | C₂H₅ | S | |
| C₂H₅ | sec. C₄H₉S | C₂H₅O | C₂H₅ | S | |
| C₂H₅ | Cl—CH₂—CH₂—S | C₂H₅O | C₂H₅ | S | |
| (n)C₃H₇ | CH₃S | C₂H₅O | C₂H₅ | S | $n_D20 : 1.5075$ |
| (n)C₃H₇ | CH₃S | CH₃O | CH₃ | S | |
| (n)C₃H₇ | CH₃S | (n)C₃H₇S | C₂H₅ | S | $n_D20 : 1.5382$ |
| (n)C₃H₇ | CH₃S | C₂H₅ | C₂H₅ | S | |
| (n)C₃H₇ | C₂H₅S | C₂H₅O | C₂H₅ | S | |
| (n)C₃H₇ | C₂H₅S | CH₃O | CH₃ | S | |
| (n)C₃H₇ | (n)C₃H₇S | C₂H₅O | C₂H₅ | S | |
| (n)C₃H₇ | (n)C₃H₇S | CH₃O | CH₃ | S | |
| (n)C₃H₇ | (n)C₃H₇S | (n)C₃H₇S | C₂H₅ | S | |
| (n)C₃H₇ | (n)C₃H₇S | C₂H₅ | C₂H₅ | S | |
| (n)C₃H₇ | (i)C₃H₇S | C₂H₅O | C₂H₅ | S | |
| (n)C₃H₇ | (n)C₄H₉S | C₂H₅O | C₂H₅ | S | |
| (n)C₃H₇ | (i)C₄H₉S | C₂H₅O | C₂H₅ | S | |
| (n)C₃H₇ | sec. H₄H₉S | C₂H₅O | C₂H₅ | S | |
| (i)C₃H₇ | CH₃S | CH₃O | CH₃ | S | $n_D20 : 1.5215$ |
| (i)C₃H₇ | CH₃S | (n)C₃H₇S | C₂H₅ | S | |
| (i)C₃H₇ | CH₃S | (n)C₄H₉S | C₂H₅ | S | |
| (i)C₃H₇ | CH₃S | (n)C₅H₁₁S | C₂H₅ | S | |
| (i)C₃H₇ | CH₃S | C₂H₅S | C₂H₅ | S | |
| (i)C₃H₇ | CH₃S | C₂H₅ | C₂H₅ | S | |
| (i)C₃H₇ | CH₃S | CH₃ | C₂H₅ | S | |
| (i)C₃H₇ | CH₃S | CH₃ | (n)C₃H₇ | S | |
| (i)C₃H₇ | CH₃S | C₆H₅ | C₂H₅ | S | |
| (i)C₃H₇ | CH₃S | (n)C₃H₇S | C₂H₅ | O | |
| (i)C₃H₇ | CH₃SO | C₂H₅O | C₂H₅ | S | |
| (i)C₃H₇ | CH₃SO | (n)C₃H₇S | C₂H₅ | S | |
| (i)C₃H₇ | CH₃SO | C₂H₅ | C₂H₅ | S | |
| (i)C₃H₇ | CH₃SO₂ | C₂H₅O | C₂H₅ | S | |
| (i)C₃H₇ | CH₃SO₂ | (n)C₃H₇S | C₂H₅ | S | |
| (i)C₃H₇ | CH₃SO₂ | C₂H₅ | C₂H₅ | S | |
| (i)C₃H₇ | C₂H₅S | C₂H₅O | C₂H₅ | S | $n_D20 : 1.5054$ |
| (i)C₃H₇ | C₂H₅S | CH₃O | CH₃ | S | |
| (i)C₃H₇ | C₂H₅S | C₂H₅ | C₂H₅ | S | |
| (i)C₃H₇ | (n)C₃H₇S | C₂H₅O | C₂H₅ | S | |
| (i)C₃H₇ | (n)C₃H₇S | CH₃O | CH₃ | S | |
| (i)C₃H₇ | (i)C₃H₇S | C₂H₅O | C₂H₅ | S | $n_D20 : 1.4998$ |
| (i)C₃H₇ | (i)C₃H₇S | (n)C₃H₇S | C₂H₅ | S | |
| (i)C₃H₇ | (i)C₃H₇S | C₂H₅ | C₂H₅ | S | $n_D20 : 1.5092$ |
| (i)C₃H₇ | Cl—CH₂—CH₂S | C₂H₅O | C₂H₅ | S | |
| (i)C₃H₇ | Cl—CH₂—CH₂S | CH₃O | CH₃ | S | |
| (i)C₃H₇ | (n)C₄H₉S | C₂H₅O | C₂H₅ | S | |
| (i)C₃H₇ | (n)C₄H₉S | CH₃O | CH₃ | S | |
| (i)C₃H₇ | (n)C₄H₉S | (n)C₃H₇S | C₂H₅ | S | |
| (i)C₃H₇ | (n)C₄H₉S | C₂H₅ | C₂H₅ | S | |
| (i)C₃H₇ | (n)C₅H₁₁S | C₂H₅O | C₂H₅ | S | |
| (i)C₃H₇ | (n)C₁₂H₂₅S | C₂H₅O | C₂H₅ | S | |
| (i)C₃H₇ | CH₃SO | CH₃O | CH₃ | S | |
| (i)C₃H₇ | CH₃SO₂ | CH₃O | CH₃ | S | |
| (i)C₃H₇ | C₆H₅-S | C₂H₅O | C₂H₅ | S | $n_D20 : 1.5395$ |
| (i)C₃H₇ | C₆H₅-SO | C₂H₅O | C₂H₅ | S | |

-continued

| R₁ | R₂ | R₃ | R₄ | X | Physical data |
|---|---|---|---|---|---|
| (i)C₃H₇ | -SO₂ | C₂H₅O | C₂H₅ | S | |
| (i)C₃H₇ | -S | (n)C₃H₇S | C₂H₅ | S | |
| (i)C₃H₇ | -S | C₂H₅ | C₂H₅ | S | |
| (n)C₄H₉ | CH₃S | C₂H₅O | C₂H₅ | S | |
| (n)C₄H₉ | CH₃S | CH₃O | CH₃ | S | |
| (n)C₄H₉ | CH₃S | (n)C₃H₇S | C₂H₅ | S | |
| (n)C₄H₉ | C₂H₅S | C₂H₅O | C₂H₅ | S | |
| (n)C₄H₉ | (i)C₃H₇S | C₂H₅O | C₂H₅ | S | |
| (i)C₄H₉ | CH₃S | C₂H₅O | C₂H₅ | S | |
| (i)C₄H₉ | CH₃S | CH₃O | CH₃ | S | |
| (i)C₄H₉ | CH₃S | (n)C₃H₇S | C₂H₅ | S | |
| (i)C₄H₉ | CH₃S | C₂H₅ | C₂H₅ | S | |
| (i)C₄H₉ | C₂H₅S | C₂H₅O | C₂H₅ | S | |
| (sec.)C₄H₉ | CH₃S | C₂H₅O | C₂H₅ | S | |
| (sec.)C₄H₉ | CH₃S | CH₃O | CH₃ | S | |
| (sec.)C₄H₉ | CH₃S | (n)C₃H₇S | C₂H₅ | S | |
| (sec.)C₄H₉ | CH₃S | C₂H₅ | C₂H₅ | S | |
| (sec.)C₄H₉ | CH₃S | CH₃ | C₂H₅ | S | |
| (sec.)C₄H₉ | CH₃S | CH₃ | (n)C₃H₇ | S | |
| (sec.)C₄H₉ | C₂H₅S | C₂H₅O | C₂H₅ | S | |
| (sec.)C₄H₉ | (i)C₃H₇S | C₂H₅O | C₂H₅ | S | |
| (t)C₄H₉ | CH₃S | C₂H₅O | C₂H₅ | S | |
| (t)C₄H₉ | CH₃S | CH₃O | CH₃ | S | |
| (t)C₄H₉ | CH₃S | (n)C₃H₇S | C₂H₅ | S | |
| (t)C₄H₉ | CH₃S | C₂H₅ | C₂H₅ | S | |
| (t)C₄H₉ | C₂H₅S | C₂H₅O | C₂H₅ | S | |
| (t)C₄H₉ | C₂H₅S | CH₃O | CH₃ | S | |
|  | CH₃S | C₂H₅O | C₂H₅ | S | |
|  | CH₃S | CH₃O | CH₃ | S | |
|  | CH₃S | (n)C₃H₇S | C₂H₅ | S | |
|  | CH₃S | C₂H₅ | C₂H₅ | S | |
|  | C₂H₅S | C₂H₅O | C₂H₅ | S | |
|  | C₂H₅S | (n)C₃H₇S | C₂H₅ | S | |
|  | CH₃S | C₂H₅O | C₂H₅ | S | |
|  | CH₃S | CH₃O | CH₃ | S | |
|  | CH₃S | (n)C₃H₇S | C₂H₅ | S | |
|  | CH₃S | C₂H₅ | C₂H₅ | S | |
|  | C₂H₅S | C₂H₅O | C₂H₅ | S | |
|  | CH₃S | C₂H₅O | C₂H₅ | S | |
|  | CH₃S | CH₃O | CH₃ | S | |
|  | CH₃S | (n)C₃H₇S | C₂H₅ | S | |
|  | CH₃S | C₂H₅ | C₂H₅ | S | |
|  | CH₃S | CH₃ | (n)C₃H₇ | S | |
|  | C₂H₅S | C₂H₅O | C₂H₅ | S | |
|  | C₂H₅S | CH₃O | CH₃ | S | |
|  | CH₃S | C₂H₅O | C₂H₅ | S | |
|  | CH₃S | CH₃O | CH₃ | S | |
|  | CH₃S | (n)C₃H₇S | C₂H₅ | S | |

-continued

| R₁ | R₂ | R₃ | R₄ | X | Physical data |
|---|---|---|---|---|---|
| Ph-CH(CH₃)- | CH₃S | C₂H₅ | C₂H₅ | S | |
| Ph- | CH₃S | CH₃O | CH₃ | S | |
| Ph- | CH₃S | (n)C₃H₇S | C₂H₅ | S | $n_D20 : 1.5891$ |
| Ph- | CH₃S | CH₃ | C₂H₅ | S | |
| Ph- | CH₃S | CH₃ | (n)C₃H₇ | S | |
| Ph- | CH₃S | (n)C₃H₇S | C₂H₅ | O | |
| Ph- | CH₃SO | C₂H₅O | C₂H₅ | S | $n_D20 : 1.5551$ |
| Ph- | CH₃SO | CH₃O | CH₃ | S | |
| Ph- | CH₃SO | (n)C₃H₇S | C₂H₅ | S | |
| Ph- | CH₃SO | C₂H₅ | C₂H₅ | S | |
| Ph- | CH₃SO₂ | C₂H₅O | C₂H₅ | S | $n_D20 : 1.5380$ |
| Ph- | CH₃SO₂ | CH₃O | CH₃ | S | |
| Ph- | CH₃SO₂ | (n)C₃H₇S | C₂H₅ | S | |
| Ph- | CH₃SO₂ | C₂H₅ | C₂H₅ | S | |
| Ph- | C₂H₅S | C₂H₅O | C₂H₅ | S | $n_D20 : 1.5556$ |
| Ph- | C₂H₅S | CH₃O | CH₃ | S | |
| Ph- | C₂H₅S | (n)C₃H₇S | C₂H₅ | S | |
| Ph- | C₂H₅SO | C₂H₅O | C₂H₅ | S | |
| Ph- | C₂H₅SO | CH₃O | CH₃ | S | |
| Ph- | (i)C₃H₇S | C₂H₅O | C₂H₅ | S | $n_D20 : 1.5515$ |
| Ph- | (i)C₃H₇S | CH₃O | CH₃ | S | |
| Ph- | (i)C₃H₇S | (n)C₃H₇S | C₂H₅ | S | $n_D20 : 1.5757$ |
| Ph- | (i)C₃H₇S | C₂H₅ | C₂H₅ | S | |
| Ph- | (n)C₄H₉S | C₂H₅O | C₂H₅ | S | $n_D20 : 1.5478$ |
| Ph- | (n)C₄H₉S | CH₃O | CH₃ | S | |
| Ph- | (sec.)C₄H₉S | CH₃O | CH₃ | S | |
| Cl-Ph- | CH₃S | C₂H₅O | C₂H₅ | S | |
| Cl-Ph- | CH₃S | CH₃O | CH₃ | S | |

-continued

| R₁ | R₂ | R₃ | R₄ | X | Physical data |
|---|---|---|---|---|---|
|  | CH₃S | (n)C₃H₇S | C₂H₅ | S | |
|  | CH₃S | C₂H₅ | C₂H₅ | S | |
|  | CH₃SO | C₂H₅O | C₂H₅ | S | |
|  | CH₃SO₂ | C₂H₅O | C₂H₅ | S | |
|  | C₂H₅S | C₂H₅O | C₂H₅ | S | |
|  | CH₃S | C₂H₅O | C₂H₅ | S | |
|  | CH₃S | C₂H₅O | C₂H₅ | S | |
|  | CH₃S | C₂H₅O | C₂H₅ | S | |
|  | CH₃S | (n)C₃H₇S | C₂H₅ | S | |
|  | CH₃S | C₂H₅O | C₂H₅ | S | |
|  | CH₃S | (n)C₃H₇S | C₂H₅ | S | |

EXAMPLE 3

A. Insecticidal stomach poison action

Tobacco and potato plants were sprayed with a 0.05% aqueous active substance emulsion (obtained from a 10% emulsifiable concentrate).

After the drying of the coating, Egyptian cotton leaf worms (Spodoptera litoralis) were placed on the tobacco plants, and Colorada beetle larvae (Leptinotarsa decemlineata) on the potato plants. The test was carried out at 24°C. with 60% relative humidity.

The compounds according to Example 2 exhibited in the above test stomach poison action against *Spodoptera litoralis* and *Leptinotarsa decemlineata*.

B. Systemic insecticidal action

In order to determine the systemic action, rooted bean plants (*Vicia faba*) were placed into a 0.01% aqueous active substance solution (obtained from a 10% emulsifiable concentrate). After a period of 24 hours, been aphids (*Aphis fabae*) were placed on to the parts of the plants above the soil. The insects were protected by a special device from the effect of contact and of gas. The test was carried out at 24°C with 70% relative humidity.

In the above tests, the compounds according to Example 2 exhibited stomach poison action and systemic insecticidal action.

EXAMPLE 4

Action against Chilo suppressalis

Rice plants of the type Caloro were planted, 6 plants per pot, in plastic pots have a top diameter of 17 cm, and grown to a height of ca. 60 cm. Infestation with *Chilo suppressalis* larvae ($L_1$; 3–4 mm long) was carried out 2 days after application of the active substance in granule form (amount applied 8 kg of active substance per hectare) to the paddy water. The evaluation of the insecticidal action was made 10 days after application of the granules.

The compounds according to Example 2 were effective against *Chilo suppressalis* in the above test.

EXAMPLE 5

Sterilised compost soil was homogeneously mixed with a wettable powder containing 25% of active substance, so that an applied amount of 8 kg of active substance per hectare resulted.

Young zucchetti plants (*Cucumis pepo*) were potted with the treated soil in plastic pots (three plants per pot of 7 cm diameter). The said pots were infestesd immediately afterwards with 5 *Aulacophora femoralis larvae*, 5 *Pachmoda larvae* and 5 *Chortophila larvae*, respectively. The assessment of the results was made 4, 8, 16 and 32 days after infestation with the larvae.

In the case of 80–100% destruction on the first assessment, a repeated infestation was carried out, 5 larvae being placed into the same sample of soil with 3 new zucchetti plants. Where the action was less than 80%, the remaining larvae were left in the test soil until the next control assessment. If a substance with an applied amount of 8 kg per hectare effected a 100% destruction, then subsequent tests were made with 4 and 2 kg of active substance per hectare, respectively.

The compounds according to Example 2 were effective in the above test against *Aulacophora femoralis* larvae, *Pachmoda* larvae and *Chlortophila* larvae.

EXAMPLE 6

Action against ticks

A. *Rhipicephalus bursa*

In each case, 5 adult ticks were placed into one small glass test tube and 50 tick larvae into another; the test tubes were then immersed for 1 to 2 minutes in 2 ml of an aqueous emulsion from a dilution series of 100, 10, 1 and 0.1 ppm of test substance. The tubes were then sealed with a standardised cotton plug, and inverted so that the active substance emulsion could be absorbed by the cotton wool.

An evaluation in the case of the adults was made after 2 weeks, and in the case of the larvae after 2 days. There were two repeats for each test.

The compounds according to Example 2 were effective in the above test against adults and larvae of *Rhipicephalus bursa*.

B. *Boophilus microplus* (larvae)

With a dilution series analogous to that in Test A, tests were carried out with 20 sensitive larvae and OP-resistant larvae, respectively (the resistance is with respect to diazinon compatibility).

The compounds according to Example 2 were effective in these tests against adults and larvae of *Rhipicephalus bursa* and against sensitive and OP-resistant larvae, respectively, of *Boophilus microplus*.

EXAMPLE 7

*Acaricidal action*

*Phaseolus vulgaris* (bush beans) were infested, 12 hours before the test for acaracidal action, with an infested piece of leaf from a mass culture of *Tetranychus urticae*. The transferred mobile stages were sprayed with the emulsified test preparations from a chromatography-sprayer in a manner ensuring no running off of the spray liquor. An assessment was made after 2 to 7 days, by examination under a binocular, of the living and of the dead larvae, adults and eggs, and the results expressed in percentages. The treated plants were kept during the "holding time" in greenhouse compartments at 25°C.

The compounds according to Example 2 were effective in the above test against adults, larvae and eggs of *Tetranychus urticae*.

EXAMPLE 8

Action against soil nematodes

In order to test the action against soil nematodes the active substances were added, in the concentration stated in each case, to soil infested with root-gall-nematodes (*Meloidogyne arenaria*), and the whole intimately mixed. In the one test series, tomato seedlings were planted immediately afterwards in the thus prepared soil, and in the other test series tomatoes were planted after a waiting time of 8 days.

For an assessment of the nematicidal action, the galls present on the roots were counted 28 days after the planting and sowing, respectively.

The active substances according to Example 2 exhibited in this test a good action against *Meloidogyne arenaria*.

We claim:

1. An insecticidal, acaricidal and nematocidal composition comprising an insecticidally, acaricidally and nematocidally effective amount of a compound of the formula $$R_1-N-N \diagdown \diagup X \diagup R_3$$
$$R_2- \diagdown \diagup -O-P \diagdown OR_4$$
$$\diagdown N \diagup$$

wherein
$R_1$ represents hydrogen, $C_1$–$C_{12}$ alkyl, $C_3$–$C_8$ cycloalkyl, phenyl, phenyl substituted by methoxy, halogen or $C_1$–$C_5$ alkyl, benzyl or phenylethyl,
$R_2$ represents $C_1$–$C_{12}$ alkylthio, $C_1$–$C_{12}$ alkylsulphinyl, $C_1$–$C_{12}$ alkylsulphonyl, phenylthio, phenylsulphinyl, phenylsulphonyl, benzylthio, benzylsulphinyl or benzylsulphonyl,
$R_3$ represents $C_1$–$C_{12}$ alkyl, $C_1$–$C_{12}$ alkoxy, $C_1$–$C_{12}$ alkylthio or phenyl,
$R_4$ represents $C_1$–$C_{12}$ alkyl, and
X represents oxygen or sulphur; together with a suitable carrier therefor.

2. The composition of claim 1, wherein in said compound
$R_1$ represents hydrogen, $C_1$–$C_6$-alkyl, cyclopentyl, cyclohexyl, benzyl, phenylethyl, phenyl, 3-chlorophenyl, 3-methylphenyl, 3-methyl-4-chlorophenyl, 2-methyl-4-chlorophenyl, 4-isopropylphenyl, 3-chloro-4-methoxyphenyl or 3,4-dichlorophenyl,
$R_2$ represents $C_1$–$C_5$-alkylthio, $C_1$–$C_5$-alkylsulphinyl, $C_1$–$C_5$-alkylsulphonyl, phenylethyl, phenylsulphinyl, phenylsulphonyl or benzylthio, benzylsulphinyl, benzylsulphonyl,
$R_3$ represents methyl, ethyl, methoxy, ethoxy, $C_1$–$C_5$-alkylthio or phenyl,
$R_4$ represents methyl, ethyl or propyl, and
X represents oxygen or sulphur.

3. The composition of claim 2, wherein said compound is 0,0-Diethyl-0-[1-isopropyl-5-methylmercapto-1,2,4-triazolyl (3)]-thiophosphate.

4. The composition of claim 2, wherein said compound is 0,0-Diethyl-0-[1-methyl-5-isopropylmercapto-1,2,4-triazolyl (3)]-thiophosphate.

5. The composition of claim 2, wherein said compound is 0,0-Diethyl-0-[1-methyl-5-methylmercapto-1,2,4-triazolyl(3)]-thiophosphate.

6. The composition of claim 2, wherein said compound is 0-Ethyl-S-Propyl-0-[1-isopropyl-5-methylmercapto-1,2,4-triazolyl(3)]-dithiophosphate.

7. The composition of claim 2, wherein said compound is 0-Ethyl-S-propyl-0-[1-phenyl-5-methylmercapto-1,2,4-triazolyl (3)]-dithiophosphate.

8. The composition of claim 2, wherein said compound is 0-Ethyl-S-propyl-0-[1-methyl-5-isopropylmercapto-1,2,4-triazolyl(3)]-dithiophosphate.

9. A method for combatting insects, acaricides or nematodes which comprises applying thereto an insecticidally, acaricidally or nematocidally effective amount of a compound of the formula of claim 1.

10. A method for combatting insects, acaricides or nematodes which comprises applying thereto an insecticidally, acaricidally or nematocidally effective amount of the compound of claim 2.

11. The composition of claim 2, wherein said compound is 0,0-diethyl-0-[1-ethyl-5-methylmercapto-1,2,4-triazolyl(3)]-thiophosphate.

12. A method for combatting insects, acaricides or nematodes which comprises applying thereto an insecticidally acaricidally or nematocidally effective amount of the compound of claim 11.

* * * * *